United States Patent
Ross et al.

(10) Patent No.: US 6,290,936 B1
(45) Date of Patent: *Sep. 18, 2001

(54) SUNSCREEN WITH DISAPPEARING COLOR INDICATOR

(75) Inventors: Jamie S. Ross, Putnam, CT (US); Elaine M. Morefield, Richmond, VA (US)

(73) Assignee: Schering-Plough HealthCare Products, Inc., Memphis, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 8 days.

This patent is subject to a terminal disclaimer.

(21) Appl. No.: 08/977,325

(22) Filed: Nov. 24, 1997

Related U.S. Application Data

(60) Provisional application No. 60/032,025, filed on Nov. 25, 1996.

(51) Int. Cl.$^7$ ................ A61K 7/42; A61K 7/44; A61K 7/00; A61K 9/00
(52) U.S. Cl. ............... 424/59; 424/60; 424/400; 424/401
(58) Field of Search ............... 424/401, 59, 60, 424/400

(56) References Cited

U.S. PATENT DOCUMENTS

| | | | |
|---|---|---|---|
| 2,366,759 | 1/1945 | Thomas et al. | 167/85 |
| 2,496,270 | 2/1950 | Coler | 167/22 |
| 2,948,657 | 9/1960 | Siccama et al. | 167/90 |
| 4,954,544 | 9/1990 | Chandaria | 524/111 |
| 5,426,210 | 6/1995 | Kato | 560/55 |
| 5,523,075 | * 6/1996 | Fuerst et al. | 424/59 |
| 5,543,137 | 8/1996 | Repper et al. | 424/59 |
| 5,562,896 | 10/1996 | Repper et al. | 424/59 |
| 5,567,420 | * 10/1996 | McEleney et al. | 424/60 |
| 5,609,852 | 3/1997 | Galley et al. | 424/59 |
| 5,747,011 | * 5/1998 | Ross et al. | 424/59 |

FOREIGN PATENT DOCUMENTS

| | | | |
|---|---|---|---|
| 0 420 713 B1 | 11/1993 | (EP) . | |
| 94/26233 | * 11/1994 | (WO) | A61K/7/00 |
| WO 95/28912 | 11/1995 | (WO) . | |
| WO 96/14826 | 5/1996 | (WO) . | |

OTHER PUBLICATIONS

Fishman, "Certified dyes", Happi, p.28, Jan. 1995.*
"Concise Encyclopedia Chemistry", Walter de Gruyter, Berlin, New York, pp.437 and 438, 1994.*
Abstract of FR 2509989 Jan. 1983.
Abstract of JP 61192778 Aug. 1986.
Abstract of JP 61192780 Aug. 1986.
Abstract of JP 61192781 Aug. 1986.
Abstract of JP 8104612 Apr. 1996.
L. Calvo, "Formulating Color Cosmetics Worldwide," *Cosmetics and Toiletries*, 1994.
Packaging for "Banana Boat Aloe Vera Dry Skin Protective Body Lotion" —date unknown.
Packaging for "Oil of Olay Daily UV Protectant Beauty Fluid"–date unknown.
Packaging for "Oil of Olay Daily UV Protectant Cream"–date unknown.
Packaging for "L'Oreal Plenitude Active Daily Moisture Lotion"—date unknown.
Packaging for "Lucky Kentucky Udder–Wize Moisturizing Balm"—date unknown.

* cited by examiner

Primary Examiner—Shelley A. Dodson
Assistant Examiner—Marina Lamm
(74) Attorney, Agent, or Firm—Robert A. Franks; Joseph T. Majka

(57) ABSTRACT

A colored, sunscreen emulsion is disclosed which employs a water-soluble dye or a blend of water-soluble dyes whose color substantially disappears when the sunscreen emulsion dries after it is spread on the skin and/or is rubbed out. The coloration in the sunscreen enables the user to more effectively protect against sunburn by allowing more complete and uniform coverage of the sunscreeen on the skin. The sunscreen emulsion comprises:

a) at least one water-soluble dye that imparts a color other than white to the sunscreen emulsion, such that when the sunscreen emulsion dries after it is spread on the skin and/or is rubbed out, the color substantially disappears;

b) at least one sunscreen active in an amount effective to protect against the actinic radiation of the sun;

c) at least one emulsfier;

d) sufficient water to form the colored emulsion;

e) optionally, one or more emollients, humectants, dry-feel agents, waterproofing agents, preservatives, antioxidants, chelating agents and fragrances as well as any other class of materials whose presence may be cosmetically, efficaciously or otherwise desirable.

21 Claims, No Drawings

SUNSCREEN WITH DISAPPEARING COLOR INDICATOR

This application claims the benefit of U.S. Provisional Application No. 60/032,025 filed Nov. 25, 1996

BACKGROUND

Sunscreens are substances or compositions applied to the skin to protect the skin from sunburn caused by the sun's ultraviolet rays. When uniformly applied to the body, sunscreens can be highly effective in protecting against sunburn. However, sunscreen failure can occur when areas of the body are missed because the sunscreen is hard to see or visualize after being applied or rubbed onto the skin. Children are at greater risk of sunburn than adults, since coverage on children's skin tends to be more incomplete, uneven or inconsistent. WO 94/26233 teaches that phenolphthalein, a color indicator, can be added to sunscreens, provided the sunscreens are formulated at a pH greater than 9.0. However, phenolphthalein can induce skin rashes and eruptions. Additionally, sunscreens with this pH are highly alkaline and also can be irritating to the skin. WO 95/28912 teaches composite UV sunblock compositions that may contain colored particles. When the sunscreen of WO 95/128912 is topically applied to the skin, the sunscreen remains visibly colored. Accordingly, an approach was sought to provide a sunscreen which could be readily visualized after the sunscreen has been applied to the skin and would substantially disappear when dried on the skin and/or rubbed out on the skin.

SUMMARY OF INVENTION

It has been surprisingly and unexpectedly found that although the inclusion of a water-soluble dye to a sunscreen emulsion can render the sunscreen visually colored, that such coloration would substantially disappear when the sunscreen emulsion dries after it is spread on the skin and/or is rubbed out.

Thus, in one embodiment, the present invention is directed towards a colored, sunscreen emulsion comprising:

a) at least one water-soluble dye that imparts a color other than white to the sunscreen emulsion, such that when the sunscreen emulsion dries after it is spread on the skin and/or is rubbed out, the color substantially disappears;

b) at least one sunscreen active in an amount effective to protect against the actinic radiation of the sun;

c) at least one emulsfier; and d) sufficient water to form the colored emulsion.

Preferably, the water-soluble dye is an External DC color or mixtures thereof, more preferably a mixture of Ext DC violet #2 and Ext DC red#33. Most preferably the water soluble dye is a mixture of Ext DC violet #2 and Ext DC red#33 in a ratio of 95:5, respectively. The amount of the water-soluble dye in the emulsion can range from about 0.0005 to about 0.5 weight percent of the emulsion, preferably from about 0.01 to about 0.05 weight percent of the emulsion. Also preferred is that the emulsion is an oil-in-water emulsion.

Optionally, the colored, sunscreen emulsion can contain one or more additional ingredients, including emollients, waterproofing agents, dry-feel modifiers, antimicrobial preservatives and/or fragrances.

In another embodiment, the present invention is directed towards a method for protecting the skin against sunburn comprising topically applying the sunscreen emulsion as described above to the skin.

One advantage of the present invention is that it provides a sunscreen and a method for protecting against sunburn that enables the user to apply the sunscreen more completely and uniformly to the skin, thus providing more effective protection against sunburn.

A second advantage of the present invention is that it provides a sunscreen with a color indicator which is substantially non-staining to the skin or the clothes.

A third advantage of the present invention is that it provides a colored sunscreen and a method for protecting against sunburn which is more fun for children to use because of the attactiveness and appealing nature of the color indicator.

DETAILED DESCRIPTION OF THE INVENTION

In the present specification, the terms "emulsion" and "composition" can be used interchangeably. The emulsion of the present invention contains one or more water-soluble dyes, one or more sunscreen actives, one or more emulsifiers, water; and may optionally contain one or more emollients, humectants, dry-feel agents, waterproofing agents, preservatives, antioxidants, chelating agents and fragrances as well as any other class of materials whose presence may be cosmetically, efficaciously or otherwise desirable.

Water Soluble Dyes

Certified dyes are synthetic organic coal tar derivatives which are manufactured so that each batch passes a Food & Drug Administration (FDA) purity inspection. If approved by the FDA, these dyes are certified for use in foods, drugs, cosmetics (FDC colors), drugs and foods only (DC colors), or in topically applied drugs and cosmetics (External DC colors). Certified dyes can be water soluble or lakes. Lakes are organic pigments prepared by precipitating a soluble dye on a reactive or absorbent stratum which is an essential part of the pigment's composition. Most lakes are aluminum, barium or calcium derived. These insoluble pigments are used mostly in makeup products, either powders or liquids, when a temporary color is desired that won't stain the skin (as oil-soluble dyes tend to do). The lakes are used in these products along with inorganic colors such as iron oxide, zinc oxide and titanium dioxide (the whitest white pigment).

Water soluble, certified dyes are used mostly in color products, not skin or hair, although it is possible to make a temporary hair color rinse using only certified dyes. When incorporating these dyes in an emulsion, they will be soluble in the external water phase in an oil/water system. It is useful to know the solubility properties of the certified dyes in various solvents and their stability to reactive chemicals. Table I lists some of the currently available water soluble certified dyes.

TABLE I

| WATER-SOLUBLE DYES |
|---|
| FDC Blue #1 |
| FDC Blue #2 |
| FDC Green #3 |
| FDC Red #3 |
| FDC Red #4 |
| FDC Yellow #5 |
| FDC Yellow #6 |
| DC Green #5 |

TABLE I-continued

WATER-SOLUBLE DYES

DC Red #22
DC Red #28
DC Red #33
DC Yellow #10
Ext DC Violet #2
Ext DC Yellow #7
DC Green #8
DC Orange #4
DC Yellow #8

When using these dyes in an emulsion, they can be added drop by drop from a prepared solution to obtain or to match a particular shade. Or the dyes can be premixed to a certain color and then added to the product. Below are some suggestions for premixing or blending two or more of these dyes to obtain a particular shade (Table II).

TABLE II

DYE COMBINATIONS

| | Pink | Amber | Lime | Olive Green | Beige | Dark Brown | Purple |
|---|---|---|---|---|---|---|---|
| FDC Red #3 | 95 | — | — | — | — | — | |
| FDC Yellow #5 | 5 | — | 99 | — | 88 | — | |
| DC Orange #4 | — | 93 | — | 5 | 10 | 50 | |
| DC Green #5 | — | 7 | — | 70 | — | 38 | |
| FDC Blue #1 | — | — | 1 | — | 2 | — | |
| DC Yellow #10 | — | — | — | 25 | — | — | |
| DC Red #28 | — | — | — | — | — | 12 | |
| Ext DC Violet #2 | — | — | — | — | — | — | 95 |
| Ext DC Red #33 | — | — | — | — | — | — | 5 |

The sunscreen emulsion should contain the water-soluble color dye (color indicator) in an amount sufficient to enable the sunscreen to be readily visualized (i.e. colored) when initially applied to the skin, such that when the sunscreen emulsion dries after being spread on the skin and/or is rubbed out using one's hand and/or fingers, the color substantially disappears. One or more water-soluble dyes can be employed in the composition in an amount ranging from about 0.0005 to about 0.5% by weight of the sunscreen composition, preferably from about 0.002 to about 0.2%, more preferably from about 0.01 to about 0.05%, most preferably from about 0.02 to about 0.04%. Also preferred is that the water-soluble color dye is a blend of Ext DC violet #2 (95%) and Ext DC red#3 (5%).

Sunscreen Actives

Accordingly, the compositions of the present invention can contain a sunscreening effective amount of one or more oil-soluble or water-soluble sunscreening UV-B actives or a mixture of one or more UV-B actives and one or more UV-A actives. UV-A type sunscreening actives protect against long wavelength actinic radiation of the sun in the 320 to 400 nm range and UV-B type sunscreening actives protect against shorter wavelength, actinic radiation of the sun in the 290–320 nm range.

Typical sunscreen actives include trade name of para-aminobenzoic acid up to about 15 weight percent or from about 5 to 15% in admixture with other sunscreen actives; cinoxate up to about 3 weight percent or about 1 to 3% in admixture; diethanolamine methoxycinnamate up to 10 weight percent or about 8 to 10% in admixture; digalloyl trioleate up to 5 weight percent or about 2 to 5% in admixture; dioxybenzone up to 3 weight percent alone or in admixture; ethyl 4-[bis(hydroxypropyl)]aminobenzoate up to 5 weight percent or about 1 to 5% in admixture; glyceryl aminobenzoate up to 3 weight percent or about 2 to 3% in admixture; homosalate up to 15 weight percent or about 4 to 15% in admixture; lawsone up to 0.25 weight percent with dihydroxyacetone up to 3 weight percent; menthyl anthranilate up to 5 weight percent or about 3.5 to 5% in admixture; octocrylene up to 10 weight percent or 7 to about 10% in admixture; octyl methoxycinnamate up to 7.5 weight percent or about 2 to 7.5% in admixture; octyl salicylate up to 5 weight percent or about 3 to 5% in admixture; oxybenzone up to 6 weight percent or about 2 to 6% in admixture; padimate "O" up to 8 weight percent or about 1.4 to 8% in admixture; phenylbenzimidazole sulfonic acid up to 4 weight percent or about 1 to about 4% in admixture; red veterinary petrolatum up to 95 percent or about 30 to 95% in admixture; sulisobenzone up to 10 weight percent or about 5 to 10% in admixture; titanium dioxide up to 25 weight percent or about 2 to 25% in admixture; and trolamine salicylate up to 12 weight percent or about 5 to 12% in admixture.

Typical suitable UV-B type sunscreening actives include benzophenone-3, benzophenone-8, substituted para-aminobenzoates, e.g., alkyl esters of para-methoxycinnamate, octyl methoxycinnamate and octyl para-methoxycinnamate, available from Givaudan Corp., Clifton, N.J. 07104 under the tradename Parsol MCX and usually present in the range of about 2 to 7.5 weight percent or or octyl salicylate available from Harmann and Riemer, Springfield, N.J., 07081, usually in the range of about 3 to 5 weight percent. The amount of UV-B type sunscreening active should be sufficient to give an SPF of at least 2 to 15.

Typical suitable UV-A type sunscreening actives include oxybenzone, usually in the range of about 2 to about 6 weight percent. Sunscreen emulsions containing mixtures of UV-B and UV-A type sunscreen actives should be sufficient to provide an SPF of 2 to 50.

Except as noted otherwise, one or more sunscreen actives can be employed in the present composition in amounts up to 35 weight percent, preferably about 12 to about 30 weight percent of the sunscreen composition, more preferably from about 5 to about 15 weight percent.

Emulsions/Emulsifiers

A stable emulsion is a mixture of two immiscible liquids, i.e. liquids that are not mutually soluble, but in the presence of an emulsifier, are mechanically agitated and shaken so thoroughly together that one liquid forms drops in the other one, giving the mixture the appearance of a homogeneous liquid. Liquids can include materials which are solid or solid-like at room temperature, but will liquify at a higher temperature during processing. The presence of an emulsifier enables one of the immiscible liquids to remain in a continuous form, while allowing the other immiscible liquid to remain in a dispersed droplet form. Thus, one function of an emulsifier, a stabilizing compound, is to assist in the production of a stable emulsion. A secondary function of emulsifiers is to provide a thickening or "bodying" to an emulsion. Typically, emulsifiers are molecules with non-polar and polar parts that are able to reside at the interface of the two immiscible liquids. As used herein in reference to the water-in-oil emulsifiers, the term "HLB value" means the hydrophile/lipophile balance. The HLB value has been used by those skilled in the emulsion art for selecting emulsifiers useful for preparing, inter alia, water-in-oil emulsions. See U.S. Pat. No. 4,177,259 and references cited therein.

An oil-in-water (o/w) emulsion is a mixture where oil droplets (the discontinuous phase) are dispersed in water (a continuous aqueous phase). A water-in-oil (w/o) emulsion is a mixture where water droplets (the discontinuous phase) are dispersed in oil (a continuous oil phase). Preferably the composition of the present invention is an oil-in-water emulsion where the oil-soluble actives are dispersed in the oil phase, prior to mixture with the water phase. The type of emulsion, oil-in-water (o/w) or water-in-oil (w/o) formed, is sometimes determined by the volume ratio of the two liquids provided the ratio is sufficiently high. For example, with 5% water and 95% oil (an o/w phase ratio of 19), the emulsion likely will become w/o. For moderate ratios (<3), the type of emulsion is decided by several factors, such as order of addition or type of emulsifier. One liquid slowly added to a second liquid with agitation usually results in the second liquid being the continuous phase. Another factor is preferred solubility of the emulsifier, the phase in which the emulsifier is soluble most probably is continuous.

More complex emulsions such as double emulsions are formed where an emulsion is dispersed in an continuous phase. For example, in an oil in-water-in oil (o/w/o) emulsion, the water in a continuous water phase containing dispersed oil droplets, are themselves dispersed in a continuous oil phase. Similarly, in a water-in oil-in water (w/o/w) emulsion, the oil in a continuous phase containing dispersed water droplets, are themselves dispersed in a continuous water phase. These more complex emulsions find use as a system for slow delivery, extraction, etc.

Typical suitable emulsifiers having an HLB value about 1 to about 7 include sorbitan monooleate, sorbitan sesquioleate, sorbitan isostearate, sorbitan trioleate, PEG-22/dodecyl glycol copolymer, PEG-45/dodecyl glycol copolymer, polyglyceryl-3-diisostearate, polyglycerol esters of oleic/isostearic acid, polyglyceryl-6 hexaricinolate, polyglyceryl-4 oleate, polyglyceryl-4 oleate/PEG-8 propylene glycol cocoate, oleamide DEA, sodium glyceryl oleate phosphate and hydrogenated vegetable glycerides phosphate.

Other emulsifiers useful in the present invention may be non-ionic, liquid or solid at room temperature and preferably compatible, i.e., soluble and stable with emollients. Preferred emulsifiers have a HLB value of less than about 5, e.g., sorbitan sequioleate (HLB value is 3.7), sorbitan monooleate (HLB value is 4.3) and sorbitan trioleate (HLB value is 1.8). Other preferred emulsifiers include polymeric emulsifiers such as copolymers of $C_{10}$–$C_{30}$ alkyl acrylates and one or more monomers of acrylic acid or methacrylic acid, also known as Pemulen® TR1 and TR2, trademark of B. F. Goodrich Inc., Cincinnati, Ohio. Other emulsifiers include sorbitan esters such as sorbitan isostearate available as Crill 6, tradename of Croda Inc. of New York, N.Y.; polyglyceryl-3 distearate available as Cremophor, tradename of tradename of BASF, Parsippany N.J.; and carbomer, which is a homopolymer of acrylic acid crosslinked with an allyl ether of sucrose, available as Carbopol 941, tradename of B. F. Goodrich, Cleveland, Ohio; and surfactants such as such as DEA-cetyl phosphate, also known as Amphisol®, trademark of Bemel Chemical Co., Englewood, N.J.

During preparation of the emulsion, an acid or a base may be added to adjust the pH of one or more ingredients, e.g. to adjust the viscosity of a polymeric thickener, prior to its inclusion in the sunscreen composition. For example, triethanolamine, a base, can be used to increase the pH of the water phase and consequently, modify the desired viscosity of the emulsion. The sunscreen can have a pH of about 6.5 to about 8, preferably from about 6.5 to about 7.5, more preferably the pH of the sunscreen is neutral, i.e. about 7.0.

Conveniently, one or more emulsifiers can be used in the compositions of the present invention in amounts ranging from about 0.05 to about 20 weight percent of emulsion, preferably from about 0.1 to about 15%, more preferably from about 5 to about 10%.

Water

Water is employed in amounts effective to form the emulsion. For hydrophilic or water-loving ingredients, e.g., emulsifiers, emollients, etc., the amount of water should be sufficient to at least solubilize these ingredients. For hydrophobic or water-repelling ingredients, the water should be employed in amounts to serve as the continuous phase of the emulsion, at least for oil-in water emulsions. Thus, amount of water in the emulsion or composition can range from about 2 to 95 weight %, preferably from 50 to 85%.

Emollients

An emollient is an oleaginous or oily substance which helps to smooth and soften the skin, and may also reduce its roughness, cracking or irritation. Typical suitable emollients include mineral, oil, having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil.

Other suitable emollients include squalane, castor oil, polybutene, odorless mineral spirits, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate which is commercially available as Lexol EHP, tradename of Inolex Co. of Philadelphia, Pa., isopropyl myristate, hexadecyl stearate, butyl stearate, decyl oleate, acetyl glycerides, the octanoates and benzoates of ($C_{12}$ –$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients which are solids or semi-solids at ambient temperatures may be use in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the sunscreen emulsion in an amount ranging from about 10 to about 50 weight %, preferably about 20 to about 40%.

Humectants

A humectant is a moistening agent that promotes retention of water due to its hygroscopic properties. Suitable humectants include glycerin, polymeric glycols such as poyethylene glycol and polypropylene glycol, and sorbitols such as sorbitol solution. One or more humectants can optionally be included in the in the sunscreen in amounts from about 1 to 10 weight %.

Dry-feel Modifier

A dry-feel modifier is an agent which when added to a emulsion, imparts a "dry feel" to the skin when the emulsion dries. Dry-feel modifiers may also reduce sunscreen migration on the skin. Dry feel modifiers can include starches, talc, kaolin, chalk, zinc oxide, silicone fluids, inorganic salts such as barium sulfate and sodium chloride, $C_6$ to $C_{12}$ alcohols such as octanol; sulfonated oils; surface treated silica, precipitated silica, fumed silica such as Aerosil® available from the Degussa Inc. of New York, N.Y. or mixtures thereof; dimethicone, a mixture of mixture of methylated linear siloxane polymers, available as DC200 fluid, tradename of Dow Corning, Midland, Mich. One or more dry-feel modifiers can optionally be included in the sunscreen in amounts ranging from 0.01 to about 20 weight %, preferably from about 0.5 to about 6 weight %.

Waterproofing Agents

A waterproofing agent is a hydrophobic material that imparts film forming and waterproofing characteristics to an emulsion. Typical suitable waterproofing agents include copolymers derived from polymerization of octadecene-1 and maleic anhydride in accordance with the published procedures such as those in U.S. Pat. No. 3,860,700 and Reissue No. 28,475. A preferred waterproofing agent is a polyanhydride resin, also known as PA-18, tradename of the Chevron Chemicals Co., San Francisco, Calif. Another preferred waterproofing agent is a copolymer of vinyl pyrollidone and eicosene monomers such as Ganex Polymer, tradename of ISP Inc. of Wayne, N.J.

By the term "waterproofing effective amount of at least one waterproofing agent" means the waterproofing agent(s) is used in amounts effective to allow the sunscreen to remain on the skin after exposure to circulating water for at least 80 minutes using the procedures described in "Sunscreen Drug Products for OTC Human Use", Federal Register, Vol. 43, Aug. 25, 1978, Part 2, pp 38206–38269. One or more waterproofing agents can optionally be included in the sunscreen composition in an amount ranging from about 0.01 to about 10.0 weight percent, preferably about 1.0 to about 10.0 percent.

Antimicrobial Preservative

An antimicrobial preservative is a substance or preparation which destroys, prevents or inhibits the multiplication/growth of microorganisms in the sunscreen composition and may offer protection from oxidation. Preservatives are used to make self-sterilizing, aqueous based products such as emulsions. This is done to prevent the development of microorganisms that may be in the product from growing during manufacturing and distribution of the product and during use by consumers who may inadvertently contaminate the products during normal use. Typical preservatives include the lower alkyl esters of para-hydroxybenzoates (parabens) especially, methylparaben, propylparaben, isobutylparaben and mixtures thereof, benzyl alcohol and benzoic acid. One or more antimicrobial preservatives can optionally be included in the sunscreen composition in an amount ranging from about 0.001 to about 10 weight percent, preferably about 0.05 to about 2 percent.

Antioxidants

An antioxidant is a natural or synthetic substance added to the sunscreen to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA )(usually as a mixture of ortho and meta isomers), butylated hydroxytoluene (BHT), nordihydroguaiaretic acid, vitamin E, vitamin E acetate, vitamin C and alkylated parabens such as methylparaben and propylparaben. One or more antioxidants can optionally be included in the sunscreen composition in an amount ranging from about 0.001 to about 5 weight percent, preferably about 0.05 to about 2 percent.

Chelating Agents

Chelating agents are substances used to chelate or bind metallic ions with a certain heterocylic ring structure so that the ion is held by chemical bonds from each of the participating ring. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.1 weight percent.

Fragrances

Fragrances are aromatic compounds which can impart an aesthetically pleasing aroma to the sunscreen composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. One or more fragrances can optionally be included in the sunscreen composition in an amount ranging from about 0.001 to about 10 weight percent, preferably about 0.05 to about 5 percent.

Dispensers

The sunscreen emulsions of the present invention containing the disappearing color indicator can be stored or dispensed in any container suitable for convenient delivery, i.e. pouring or spraying. Such containers can include but are not limited to jars, bottles, lotion pumps, pump spray bottles and aerosols.

Definitions and suppliers of the ingredients used in the following illustrative examples may be found in the CTFA Cosmetic Ingredient Dictionary, published by the Cosmetic, Toiletry and Fragrance Association, Inc., 1110 Vermont Avenue, NW, Wash. D.C. 20005, Third Edition 1982. Proportions are by percent weight.

| Ingredients | Theoretical Quantity (g) | Weight percent (%) |
|---|---|---|
| Part A - Oil soluble ingredients | | |
| Stearic Acid | 150.0 | 15.00 |
| Parsol MCX | 50.0 | 5.00 |
| Oxybenzone | 30.0 | 3.00 |
| Jojoba oil | 0.5 | 0.05 |
| Aloe Vera Lipoquinone | 0.5 | 0.05 |
| Part B - Water soluble ingredients | | |
| Water | 628.0 | 62.88 |
| Sorbitol Solution 70% | 20.0 | 2.00 |
| Triethanolamine, 99% | 120.0 | 12.00 |
| Violet D&C Dye Blend | 0.2 | 0.02 |

Admix the ingredients of Part A in a stainless steel pot at a temperature of 82–85° C. (160–165° F.) equipped with a stirrer until a homogeneous admixture is formed. Similarly admix the ingredients of Part B in a separate pot. Using vigorous stirring, add Part B to Part A until an emulsion is formed having a violet color and cool to room temperature. The D&C Dye Blend imparts a violet color to the sunscreen emulsion, enabling it to be readily visualized when the sunscreen emulsion is initially applied to the skin. When the colored sunscreen dries after it is spread on the skin and/or is rubbed out, the violet color substantially disappears.

| Ingredients | Theoretical Quantity (g) | Weight percent (%) |
|---|---|---|
| Part A - Water soluble ingredients | | |
| Water | 662.20 | 66.22 |
| Pemulen TR-1 | 4.00 | 0.40 |
| Polyethylene Glycol | 50.00 | 5.00 |
| Disodium EDTA | 0.10 | 0.01 |
| Amphisol | 3.50 | 0.35 |
| Triethanolamine, 99% | 5.00 | 0.50 |
| DC Green #5 | 0.20 | 0.02 |
| Part B - Oil soluble ingredients | | |
| Lexol EHP | 80.00 | 8.00 |
| Parsol MCX | 67.50 | 6.75 |
| Oxybenzone | 30.00 | 3.00 |
| Jojoba Oil | 1.00 | 0.10 |
| Vit E Acetate | 1.00 | 0.10 |
| Aloe Vera Lipoquinone | 1.00 | 0.10 |
| Methylparaben | 3.00 | 0.30 |
| Propylparaben | 1.00 | 0.10 |
| Ganex Polymer | 20.00 | 2.00 |
| Aerosil | 10.00 | 1.00 |
| Part C - Other ingredients | | |
| Fragrance | 0.50 | 0.05 |
| Starch | 50.00 | 5.00 |
| Benzyl Alcohol, NF | 10.00 | 1.00 |

Admix the ingredients of Part A in a stainless steel pot at a temperature of 82–85° C. equipped with a stirrer until a homogeneous admixture is formed. Similarly admix the ingredients of Part B in a separate pot. Using vigorous stirring, add Part B to Part A until an emulsion is formed having a green or teal color and cool to 38° C. Stir in the ingredients of Part C until completely dissolved. When the colored sunscreen dries after it is spread on the skin and/or is rubbed out, the green or teal color substantially disappears.

| Ingredient Description | Theoretical Quantity (g) | Weight percent (%) |
|---|---|---|
| Part A - Oil soluble ingredients | | |
| Stearic Acid | 20.00 | 2.0000 |
| Crill 6 | 40.00 | 4.0000 |
| Parsol MCX | 75.00 | 7.5000 |
| Homosalate | 80.00 | 8.0000 |
| Oxybenzone | 60.00 | 6.0000 |
| Octyl salicylate | 50.00 | 5.0000 |
| Jojoba Oil | 0.50 | 0.0875 |
| Aloe Vera Lipoquinone | 0.50 | 0.0875 |
| Propylparaben | 1.00 | 0.1000 |
| Cremophor | 30.00 | 3.0000 |
| Polyanhydride Resin PA-18 | 30.00 | 3.0000 |
| D.C. 200 Fluid | 4.00 | 0.4000 |
| Vitamin E acetate | 1.00 | 0.1000 |
| Part B - Water soluble ingredients | | |
| Barium sulfate | 17.50 | 1.7500 |
| Carbopol 941 | 0.25 | 0.0250 |
| Sorbitol Solution, 70% | 50.00 | 5.0000 |
| Triethanolamine, 99% | 22.25 | 2.2500 |
| Methylparaben | 2.00 | 0.2000 |
| Disodium EDTA | 0.10 | 0.0100 |
| Water | 500.00 | 50.0000 |
| FDC Blue #1 | 0.40 | 0.0400 |
| Part C - Other ingredients | | |
| Benzyl Alcohol NF | 10.00 | 1.0000 |
| Fragrance | 6.00 | 0.6000 |

Admix the ingredients of Part A in a stainless steel pot equipped with a stirrer at a temperature of 82–85° C. until a homogeneous admixture is formed. Similarly admix the ingredients of Part B in a separate pot. Using vigorous stirring, add the admixture of Part A to Part B until an colored emulsion is formed and cool to 45° C. Stir in Part C until the ingredients are completely dissolved to give a resultant sunscreen emulsion having a blue color. When the colored sunscreen dries after it is spread on the skin and/or is rubbed out, the blue color substantially disappears.

The visualization and disappearance of the sunscreen on the skin can be evaluated using visual, chromatographic and pantone matching systems.

To evaluate the color indicator on the skin, it may be helpful to have an objective, instrumental measurement of colors and intensities. Accordingly, a method has been developed using a Minolta Chroma Meter CR-200, which uses reflected light from a surface and gives results in terms of the CIE (International Commission on Illumination) tristimulus values. These values are subsequently transformed mathematically into the $L^*$ $a^*$ $b^*$ color space, wherein the magnitudes of changes in hue and intensity of color correspond closely with those perceived by the human eye.

$L^*$, being achromatic, ranges from black ($L^*=0$) to white ($L^*=100$); this term is called 'metric lightness" and is a measure of how light or dark a color is, relative to a matching shade of gray. Hue is measured in terms of the chromaticity coordinates $a^*$ and $b^*$, where $a^*$ indicates redness ($a^*>0$) and $b^*$ indicates yellowness ($b^*>0$). The values of $a^*$ and $b^*$ can be plotted with $a^*$ as the x-axis and $b^*$ as the y axis, to give quantitative color information: "metric chroma" is the length of a line from the origin ($a^*=0, b^*=0$) to the point of a sample reading, while 'metric hue angle, is the angle between the $a^*$ axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The meter can be used to measure a base line skin tone as well as residual color left on the skin after "rub out" with a number of subjects, to establish a target for disappearance of color applied to the skin.

What is claimed is:

1. A colored sunscreen emulsion comprising:
    a) at least one water-soluble dye, in amounts sufficient to impart a color other than white to the sunscreen emulsion, which color is readily visualized by a user after the emulsion is spread on skin but, when the sunscreen emulsion dries after it is spread on skin and/or is rubbed into skin, the color substantially disappears;
    b) a waterproofing-effective amount of at least one waterproofing agent;
    c) at least one sunscreen active ingredient in an amount effective to provide a waterproof SPF value of 2 to 50;
    d) at least one emulsifier; and
    e) sufficient water to form the colored emulsion.

2. The colored, sunscreen emulsion of claim 1 wherein the water-soluble dye is an External DC color or blend of two or more External DC colors.

3. The colored, sunscreen emulsion of claim 1 wherein the water-soluble dye imparts a purple or violet color to the sunscreen emulsion.

4. The colored, sunscreen emulsion of claim 3 wherein the water-soluble dye is a mixture of Ext DC violet #2 and Ext DC red #33.

5. The colored, sunscreen emulsion of claim 1 wherein the emulsion is an oil-in-water emulsion (o/w).

6. The colored, sunscreen emulsion of claim 1 wherein the emulsion is an water-in-oil emulsion (w/o).

7. The colored, sunscreen emulsion of claim 1 wherein the emulsion is an oil-in water-in oil emulsion (o/w/o).

8. The colored, sunscreen emulsion of claim 1 wherein the emulsion is a water-in-oil-in water emulsion (w/o/w).

9. The colored, sunscreen emulsion of claim 1 having a pH of about 6.5 to about 8.

10. The colored, sunscreen emulsion of claim 1 having a pH of about 6.5 to about7.5.

11. A method for protecting the skin against sunburn comprising topically applying to the skin the colored, sunscreen emulsion of claim 1.

12. The colored sunscreen emulsion of claim 1 wherein the water-soluble dye imparts a blue color.

13. The colored sunscreen emulsion of claim 12 wherein the water-soluble dye is Blue #1, Blue #2 or a mixture thereof.

14. The colored sunscreen emulsion of claim 1 wherein the dye imparts a green or teal color.

15. The colored sunscreen emulsion of claim 1 wherein the dye is present in amounts about 0.0005 to about 0.5 percent by weight and imparts a color selected from the group consisting of purple, violet, green, yellow, red, orange, teal and blue.

16. The colored sunscreen emulsion of claim 15, wherein the dye is present in amounts about 0.002 to about 0.2 percent by weight.

17. The colored emulsion of claim 1, wherein the dye imparts a color selected from the group consisting of pink, amber, lime, olive green, beige and brown.

18. The colored emulsion of claim 1, wherein the dye is present in amounts about 0.01 to about 0.05 percent by weight and imparts a color selected from the group consisting of purple, pink, amber, lime, olive green, beige, brown, violet, green, yellow, red, orange, teal and blue.

19. The colored emulsion of claim 18, wherein the dye imparts a blue color.

20. The colored emulsion of claim 18, wherein the dye imparts a violet or purple color.

21. The colored emulsion of claim 18, wherein the dye is present in amounts about 0.02 to 0.04 percent by weight.

* * * * *